United States Patent [19]
Spencer

[11] 4,369,779
[45] Jan. 25, 1983

[54] STERILE DOCKING PROCESS, APPARATUS AND SYSTEM

[75] Inventor: Dudley W. C. Spencer, Wilmington, Del.

[73] Assignee: E. I. Du Pont de Nemours and Company, Wilmington, Del.

[21] Appl. No.: 267,291

[22] Filed: Jun. 4, 1981

Related U.S. Application Data

[63] Continuation-in-part of Ser. No. 236,855, Feb. 23, 1981, abandoned, which is a continuation-in-part of Ser. No. 167,716, Jul. 11, 1980, abandoned.

[51] Int. Cl.³ .................... A61M 5/00; B29C 27/00
[52] U.S. Cl. ..................... 128/213 A; 128/214.2; 128/247; 156/159; 156/304.2; 156/503
[58] Field of Search ............ 156/158, 159, 296, 502, 156/503, 251 M, 304.2, 304.5, 304.3, 358, 433; 128/214 D, 214.2, 213 R, 213 A; 264/248

[56] References Cited

U.S. PATENT DOCUMENTS

| | | | |
|---|---|---|---|
| 3,013,925 | 12/1961 | Larsen | 156/503 |
| 3,035,631 | 5/1962 | Knowles | |
| 3,117,903 | 1/1964 | Hix | 156/158 |
| 3,897,296 | 7/1975 | Waldrum | |
| 3,968,195 | 7/1976 | Bishop | |
| 4,149,534 | 4/1979 | Tenczar | 128/214.2 |
| 4,209,013 | 6/1980 | Alexander et al. | |
| 4,223,675 | 9/1980 | Williams | |
| 4,242,310 | 12/1980 | Greff et al. | |
| 4,288,266 | 9/1981 | Konrad et al. | 156/304.2 |

FOREIGN PATENT DOCUMENTS 2250130 4/1974 Fed. Rep. of Germany.

OTHER PUBLICATIONS

Myhre et al., *Transfusion*, 18, No. 5, pp. 546–552, Sep.–Oct., 1978.

*Primary Examiner*—Michael W. Ball

[57] ABSTRACT

A process, apparatus and system for making a sterile connection between two thermoplastic resin tubes is disclosed. The tubes are cut by a hot cutting means so as to form a molten interface between the tubes and the cutting means. The tubes are aligned with each other and slid off an edge of the cutting means while being urged together. As the thermoplastic resin cools a sterile weld is formed. The cutting means should either be thin or have a sharp edge where the aligned tubes are slid off and joined.

24 Claims, 12 Drawing Figures

STERILE DOCKING PROCESS, APPARATUS AND SYSTEM

CROSS-REFERENCE TO RELATED APPLICATIONS

This application is a continuation-in-part of copending application Ser. No. 236,855 filed on Feb. 23, 1981 now abandoned which in turn is a continuation-in-part of application Ser. No. 167,716 filed on July 11, 1980 now abandoned.

BACKGROUND OF THE INVENTION

Field of the Invention

This invention relates to a process, apparatus and system for forming a sterile connection (sterile docking) between two tubes.

At the present time there are a number of medical and scientific procedures which require the sterile transfer of fluids from one container to another. The only truly sterile transfer system in current use involves prejoining containers with tubes and then sterilizing the entire assembly. This is inflexible and costly since new containers cannot be added and the number of joined containers needed is often not known at the time of initial filling.

An example of the need for sterile docking is in continuous ambulatory peritoneal dialysis (CAPD). This procedure is replacing dialysis of blood outside the body in membrane diffusion cells where waste products normally removed by kidneys are washed from the blood, which is then returned to the patient. Dialysis outside of the body is a time-consuming procedure and sometimes results in damage to the blood by exposure to materials and conditions external to the body. In CAPD, the patient is required to spend time only for draining spent dialysate and replacing it with a fresh solution.

The CAPD patient has a tube connected to his or her peritoneal cavity via an implanted catheter. A tube from a bag of fresh dialysis solution is connected to the patient's tube. The fresh dialysis solution is drained from the bag into the patient's peritoneal cavity where it remains for about 3–4 hours. During this treatment period, the empty bag is folded and carried by the patient who can continue with his or her normal activities. After this treatment period, the spent dialysate is drained back into the empty bag which is then disconnected from the patient's tube. A bag of fresh dialysis solution is then connected to the patient's tube and the procedure is repeated. Connection to a new bag of dialysis solution exposes the tube ends to airborne bacteria or other contamination even though precautions are taken. No satisfactory way heretofore has existed to insure sterility in spite of the elaborate and costly precautions now employed including the use of masks, gloves, gauze strips and disinfectant solutions. Usually contamination does occur to the extent that a case of peritonitis is contracted perhaps on the average once or more a year and scare tissue from it inhibits dialysis.

Truly sterile connections could minimize the occurrence of peritonitis. Also any other treatment bags, such as for an antibiotic, bacteriostat, or other medication, could be connected as desired.

A similar need for sterile docking exists for blood bags. At present, blood from a donor is drawn into a primary bag which may be joined to one or two satellite bags, all connected and sterilized before use. These satellite bags may be needed for holding blood separated components, such as plasma or platelets; treating agents, such as bases, buffers, stabilizers for cell metabolism, other preservatives, or rejuvenants; or washes to remove a treating agent or other contaminant. Actually, it is not feasible to have preconnected bags for all the treatments which may be desired. Supplemental treatments such as fresh preservative cannot now be added sterilely during bag storage by any commercially acceptable procedure. In addition, to avoid the expense of unused satellite bags, the number of such bags is chosen based on limited, predicted needs. The inability to forecast needs well adds greatly to inventory requirements and complicates scheduling of blood donations.

Currently, very limited use is made of quality control as a time assay of the quantity and quality of components in separated blood factions. The main reason for the current limited use is that heretofore any entry into a sterile blood unit exposed the blood to bacteria, thereby requiring that the blood be used within 24 hours from entry. Hence, although the viability of stored blood components can be extended by supplemental treatments, such as adding a preservative during storage, such treatments are usually not effected.

Moreover, the primary blood bag contains anticoagulant which can be sterilized only by heat (steam); thus all preconnected bags are also sterilized by wet-sterilization techniques, i.e., steam or hot water in an autoclave apparatus. These bags are made of plasticized polyvinyl chloride (PVC), although other materials are known to be useful for constructing bags which are favorable for other reasons, such as greater oxygen permeability. Since many such materials, e.g., oxygen permeable polyethylene, are not steam sterilizable, they are not now used in preconnected systems.

A sterile docking means would permit one to effect whatever processing is desired without comprising sterility, limiting storage life or requiring the preconnection of a multitude of bags, all wet-sterilizable, without knowing which, if any, will be used.

References

U.S. Pat. No. 3,968,195 discloses a method for making a sterile connection between two rigid tubes the free ends of which have thermoplastic diaphragms which seal off the free ends. When a sterile connection between the free ends of the two tubes is desired, the free ends of each rigid tube are aligned while being spaced slightly apart, and each thermoplastic diaphragm is opened by heating. The free ends of the rigid tubes are then brought into contact and held in position under a slight pressure while the thermoplastic material cools and solidifies, thereby creating a permanent connection. This process requires tubes which have low-melting thermoplastic diaphragms on the ends which can only be used once, i.e., another connection to the same tubing cannot be made. The method of U.S. Pat. No. 3,968,195 has not been adopted because great skill would be required to maintain the ends in a flame or heated air jet so no bacteria can survive but without melting the tubes.

U.S. Pat. No. 3,897,296 discloses a method of welding two plastic surfaces together by juxtapositioning the surfaces, heating the surfaces to a temperature approaching the flash point of the plastic surfaces to liquefy the surfaces, removing a portion of the liquefied surfaces to expose unoxidized surfaces therebeneath and immediately bringing the unoxidized surfaces into abutment with one another. This reference is silent as to cutting a tube as well as forming a sterile dock.

"An Aseptic Fluid Transfer System for Blood and Blood Components," B. A. Myhre et al, Transfusion, Vol. 18, No. 5, pp. 546-552, September-October 1978, describes a process for heat sealing two aseptic fluid transfer system (AFTS) units together. The AFTS units contain a layer of Kapton ® film (an aromatic polyimide resin which is stable at relatively high temperatures).

A pair of dies, one of which is flat and one of which has a raised "H" shaped area, are brought together under a pressure of 100 psi (6.9×10⁶ dynes per square centimeter) with the AFTS units disposed between the dies. The temperatures of the dies is raised to 200° C. (392° F.) over a period of 45 seconds. The dies are withdrawn and upon removal of the AFTS units from the dies, the AFTS units are heat sealed together by a seal surrounding an opening between the AFTS units. Blood bags constructed with an AFTS unit attached can thereby be joined. This system is slow and requires specially constructed units that can only be used once.

SUMMARY

The present invention relates to a process, apparatus and system for cutting and joining two sterile, closed end tubes or conduits using a hot cutting means while maintaining system sterility. The closed ends of the tubes to be joined are sequentially or simultaneously cut by the cutting means with molten polymer sealing each tube end against the cutting means. Seals of molten polymer hot enough to kill quickly bacteria are maintained continuously with no chance for viable airborne or surface bacteria to find their way inside either of the tubes or the joint. The tube ends are moved into alignment, the heated cutting means slid away, and the ends pushed together, all while maintaining the seals. When the joint cools, the sterile connection or docking is complete. The joint is sound and strong and a number of additional joints can be made in subsequent dockings with the same tube. This invention provides a quick, inexpensive system with no special fittings permitting maximum flexibility in processing, storing and using sterile fluids.

DETAILED DESCRIPTION OF THE INVENTION

Figure 1:
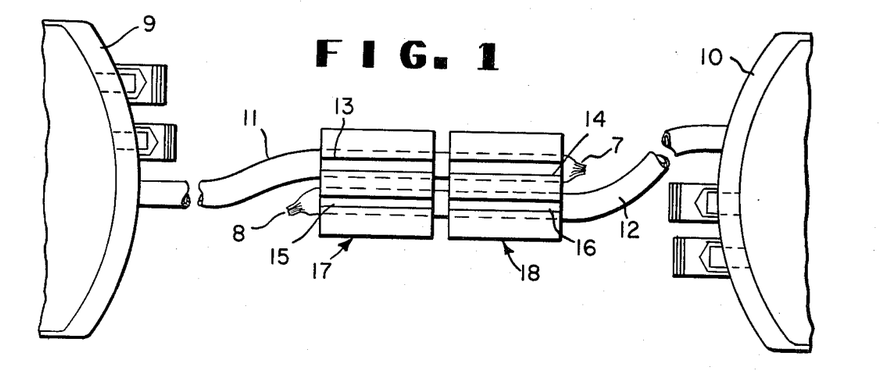
FIG. 1 is a plan view of mounting blocks used to hold two tubes which are to be joined in the starting position.

Referring now to FIG. 1 the sealed end 7 of thermoplastic tube 11 is inserted in slots 13 and 14, machined in blocks 17 and 18. The sealed end 8 of tube 12 is inserted in slots 15 and 16, machined in blocks 17 and 18. Slots 13-14 and 15-16 are aligned to receive straight tubing ends. In FIGS. 1-4, tubes 11 and 12 are connected to blood bags 9 and 10. Alternately, one of said tubes may be connected to a dialysis bag and the other to the patient's peritoneal cavity. Also, the tube which is connected to the patient's peritoneal cavity may be connected at the other end to an empty bag in lieu of having a sealed end.

Figure 2:
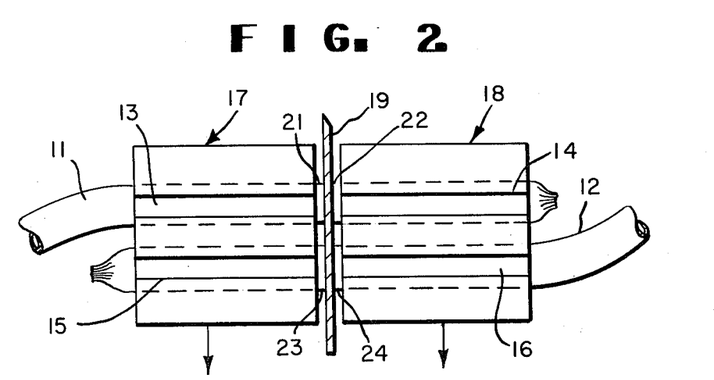
FIG. 2 is a plan view of the two tubes being severed by a hot cutting means.

Referring now to FIG. 2, the two blocks 17 and 18 have been slid in the direction shown by the arrows, relative to hot cutting means 19, which in the figure is a blade made of steel, so that the cutting means has cut (melted through) tubes 11 and 12 and there are now four molten tube interfaces 21, 22, 23 and 24 lying against hot cutting means 19. These molten interfaces 21 and 24 prevent exchange of air between the interior of tubes 11 and 12 and air outside tubes 11 and 12 as well as contamination from particles suspended in the air or on the tubing or apparatus surfaces except the hot cutting means. It is to be understood that while urging the tubes together as described later herein, momentary gaps which may occur could be tolerated.

Figure 3:
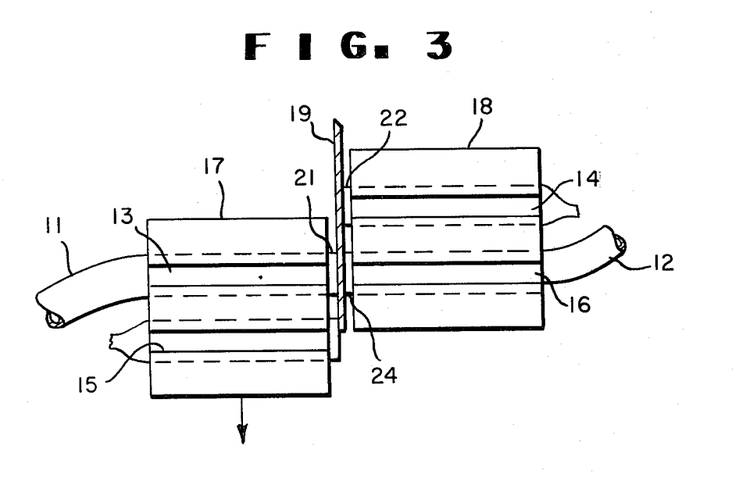
FIG. 3 is a plan view of the two tubes being repositioned and aligned opposite each other.

Referring now to FIG. 3, block 17 has been moved relative to block 18 so that slots 13 and 16 along with tubes 11 and 12 are aligned on opposite sides of the hot cutting means. Molten interface (tube end) 21 has been wiped along the surface of hot cutting means 19 during movement of the block.

Figure 4:
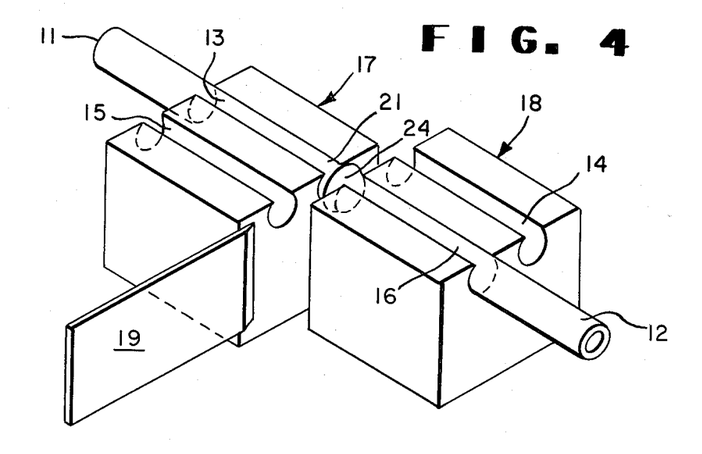
FIG. 4 is a perspective of the mounting blocks, cutting means and welded tubes.

Referring now to FIG. 4, blocks 17 and 18, with slots 13 and 16 and tubes 11 and 12 still aligned, and hot cutting means 19 have been moved relative to each other and the molten interfaces 21 and 24 have fused and thereby joined tubes 11 and 12 together. The blocks 17 and 18 holding tubes 11 and 12 were urged together by a spring (shown in FIG. 5) during the time when they and cutting means 19 were being moved relative to each other, resulting in a slight compression of the joint.

Figure 5:
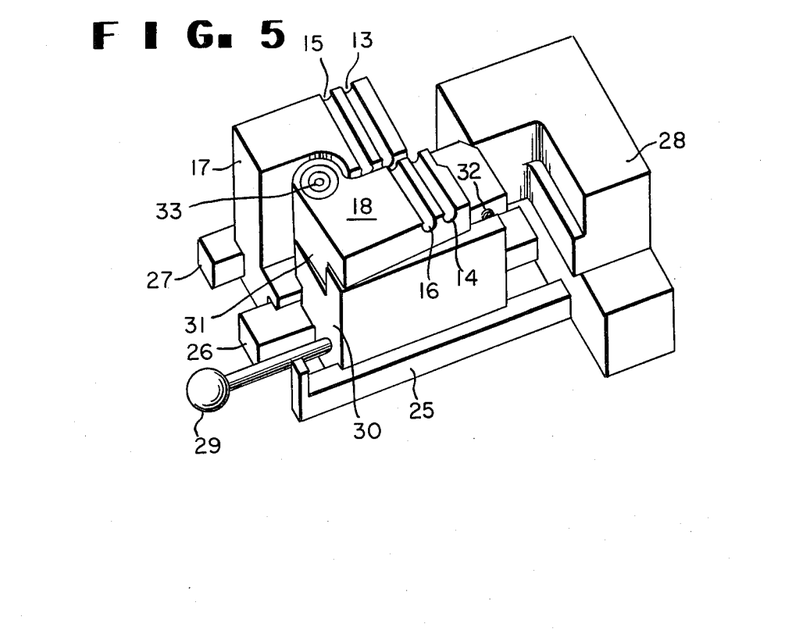
FIG. 5 is a perspective view of the mounting blocks slidably mounted on their guides.

Referring now to FIG. 5, blocks 17 and 18 are shown with slots 13 and 16 aligned and the block in the position after the weld has been made and the welded tubes removed. The blocks are shown slidably mounted in guides 25, 26 and 27. Block 18 is shown as two parts 30, 31 which are connected together by bolt 33 so as to allow rotational motion of part 31. Thereby, part 31 can be individually urged by spring 32 toward block 17 as the blocks and tubes (not shown) held thereby are withdrawn from the cutting means (not shown for clarity).

Figure 6A:
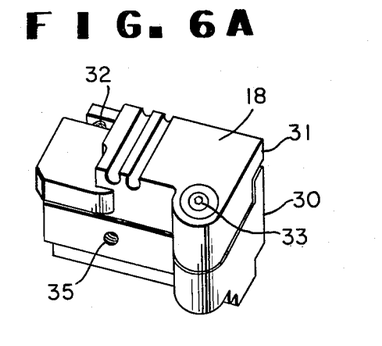
FIGS. 6A and B are perspective views of the mounting blocks.
Figure 6B:
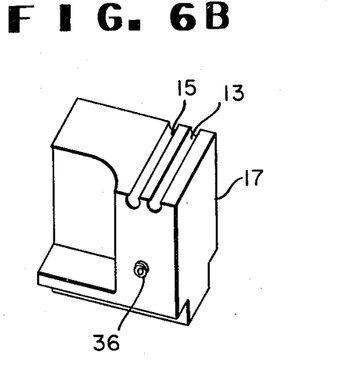
Figure 7:
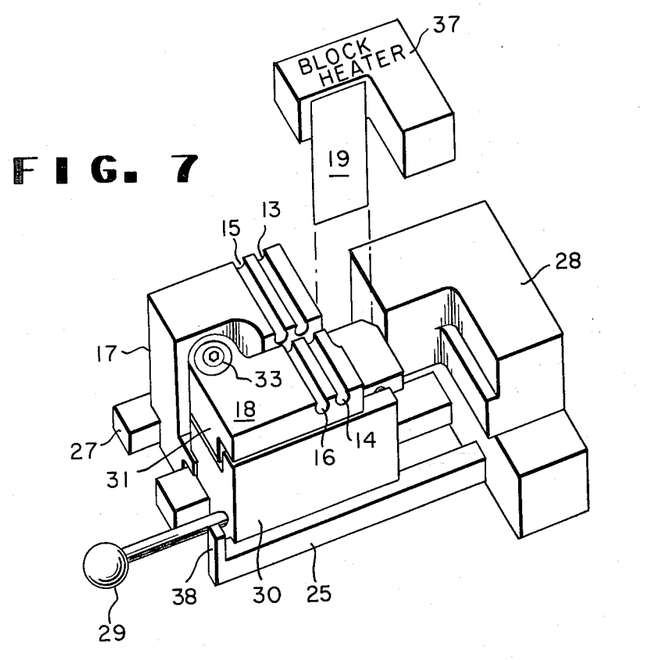
FIG. 7 is a perspective view of the mounting blocks, slidably mounted on their guides and cutting means with block heater.
Figure 8:
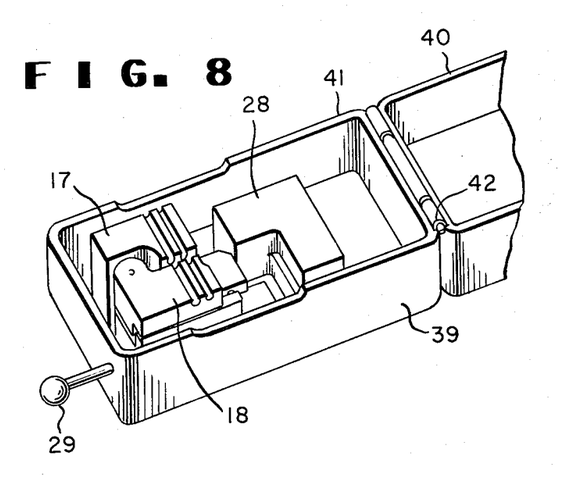
FIG. 8 is a perspective view of the mounting blocks fixedly arranged in a housing.

FIG. 5 also shows operating handle 29 and stop-block 28 against which mounting blocks 17 and 18 are pushed. Operation of this embodiment is best described by using FIGS. 5-8 along with reference to FIGS. 1-3 already described. The operator inserts tube ends in slots 13-14 and 15-16 as shown in FIG. 1. Cutting means 19 and block heater 37 shown in FIG. 7 are lowered so that cutting means 19 is positioned between stop-block 28 and mounting blocks 17 and 18 in alignment with the space between said mounting blocks. This positioning is effected by having block heater 37 and cutting means 19 fixedly arranged in the upper portion 40 of housing 39 shown in FIG. 8 and the mounting blocks, stop-block 28 and the accompanying slides fixedly arranged in a base portion 41 of housing 39 so that when the housing is closed the cutting means is properly situated. The two sections of the housing are attached by hinge 42.

Blade block heater 37 (FIG. 7) for heating the cutting means is activated. Blocks 17 and 18 shown in FIGS. 6A and B fit together so that the foremost horizontal faces are adjacent. When in the starting position, the mounting blocks are kept in a cooperative relationship by pressure fit of threaded pin 36 on block 17 into cavity 35 in block 18 (FIG. 6). The operator pushes handle 29 which moves blocks 17 and 18 together on slides 25, 26 and 27, thereby moving the tubes across hot cutting means 19 as shown in FIG. 2. Block 17 strikes stop-block 28 first thereby causing the two blocks to become sufficiently disengaged so that block 18 moves on to stop against stop-block 28. This further movement by block 18 aligns slots 13 and 16 as shown in FIG. 3, as the cut tube ends remain sealed by molten polymer against hot cutting means 19. The operator immediately withdraws handle 29 to move block 18 which is connected to the handle 29 and, by friction between the blocks through the pressure exerted by pin 36 on block 18, block 17 also. The blocks and the tube ends to be joined move back away from hot cutting means 19. As the corner of block 18 leaves the edge of block 28, spring 32 urges part 31 of block 18 to rotate slightly about bolt 33 toward block 17 so that slight compression is urged on the tube ends being joined as they slide off the edge of the hot cutting means (see FIG. 5). Stop 38 (FIG. 7) on slide 25 completes the motion of blocks and handle. The operator removes the joined tube after about 5 seconds delay for the joint to cool.

Figure 9:
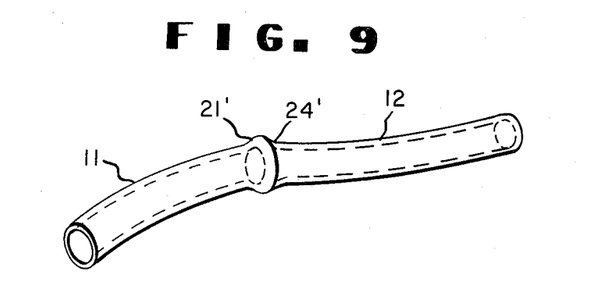
FIG. 9 is a perspective view of the welded tubes.

Referring now to FIG. 9, tubes 11 and 12 are shown joined at now fused molten interfaces 21' and 24' to form a joint which is slightly enlarged due to the pressure exerted by spring 32.

The cutting means used in the present invention can take several forms. The cutting means should have reasonably flat sides in order to maintain the molten interfaces between the tubes and the sides of the cutting means intact as the tubes are moved along the sides of the cutting means. The cutting means can be in the form of a band, a disk, wedge, knife, etc., either permanent or disposable. The cutting means should either be thin, i.e., about 5–35 mils (0.12–0.89 mm) or have a relatively sharp edge where the tubes are removed from contact therewith and joined. The cutting means can be made of any of a variety of materials, such as steel, stainless steel, silver, titanium, and a composite made according to printed circuit technology in single blades or blades mounted in a magazine.

Various heating means may be used to heat the cutting means such as electical resistance, induction, contact with a heated block, etc. The cutting means can be made self-heating by incorporating an electrical resistance heating element in its structure. Preferably, the cutting means is a strip which is indexed so that a new clear portion is presented after completion of each docking. Preferably, the strip is a laminate and, more preferably, is 9.8 mils (0.25 mm) in thickness and is constructed from a ribbon of stainless steel of 1 mil (0.025 mm) thickness etched to form a resistance heating element having on both sides the following layers: (1) a 1 mil (0.025 mm) layer of acrylic adhesive, (2) a 1 mil (0.025 mm) layer of an aromatic polyimide resin which is stable up to at least 400° C., (3) a 1 mil (0.025 mm) layer of acrylic adhesive, and (4) a ribbon of copper of 1.4 mil (0.036 mm) thickness. The laminate has a 2-mil (0.051 mm) brass jacket on its outside.

Currently-used blood and dialysis bags and tubes are made of plasticized polyvinyl chloride for flexibility, strength and steam sterilizing. Generally, for these plasticized polyvinyl chloride tubes, the cutting means will be heated to a temperature of from about 500° F. (260° C.) to 750° F. (399° C.) which is also suitable for most other thermoplastic tubing. The cutting means preferably is at a temperature high enough (1) to kill rapidly (less than one second) any bacteria or bacterial spores on the outside surface of the tubes and (2) to melt rapidly the thermoplastic resin from which the tubes are formed. The tubes are heat-sealed closed at their ends or connected to a bag. The tubes and whatever bag or bags they are connected to will have been sterilized. Below about 500° F. (260° C.) bacteria and bacterial spores are not rapidly killed by the heat from the cutting means. Above about 750° F. (399° C.) most polymers such as plasticized polyvinyl chloride or polyolefins such as polypropylene or polyethylene begin to become too liquid to maintain a seal with the cutting means. About 600° F. (316° C.) is the preferred temperature for use with conventional plasticized polyvinyl chloride blood bag tubing. Another upper limit is the temperature where the resin from which the tube is made begins to degrade in the time it is exposed to the heated cutting means (about 2 seconds). For plasticized polyvinyl chloride and polyolefins the upper limit is about 300° F. (149° C.) above the melting point of the thermoplastic resin from which the tube is made.

The tube should be advanced into the cutting means at a rate such that the polymer from which the tube is fabricated melts up against the cutting means and there should be no mechanical cutting of unmolten polymer of significant visible deformation of the tube. Excessive heating times are to be avoided in order to minimize excess melting or degradation of the polymer. For conventional 165 mil (4.2 mm) outside diameter, 10 mils (0.25 mm) thick wall plasticized polyvinyl chloride blood bag tubing, a time of 0.5 to 1.5 seconds for cutting the two tubes has been found to be most satisfactory. The time for repositioning the tubes to align them is not particularly critical but should not be so fast as to disrupt the molten seal between tube and the cutting means nor so slow as to cause degraded polymer to be in the welded joint. The speed of withdrawal of the cutting means is important to minimize degradation and excess melting and 0.1 to 1 second has been found to be satisfactory. After removal of the hot cutting means, cooling of the tubes takes about 5 seconds and the tubes are then removed from the blocks.

The mounting blocks are made of heat conductive metal and serve as heat sinks to assist rapid cooling of the joint. It is necessary that the tubes be urged toward each other as the hot cutting means is removed. The space between the blocks and the hot cutting means is relatively important. For tubes of about 165 mils (4.2 mm) outside diameter, the spacing between each of the blocks and the surface of the hot cutting means should be from about 5 mils (0.13 mm) to 50 mils (1.3 mm), and the preferred spacing between the blocks and the hot cutting means being from about 10 mils (0.25 mm) to 20 mils (0.51 mm). With less than about 10 mils (0.25 mm) and especially below about 5 mils (0.13 mm) of tube protruding from a block to the hot cutting means there is too much heat loss to the block to maintain an adequate molten polymer seal required to provide a sterile connection. Above about 20 mils (0.51 mm) and especially above about 50 mils (1.3 mm) the exposed tube ends have too much flexibility and the joint may not be sterile. For tubes very much larger than 165 mils (4.2 mm) appropriately larger spacings can be used.

The tubing used should be formed of a thermoplastic resin which melts at least 50° F. below the temperature at which it begins to degrade in the time exposed to heat in the process of the present invention. The tubes to be connected are preferably of the same diameter but can have different diameters so long as a complete seal having about 50% of the original tube strength can be made. The tubes to be joined can be made of the same material or can be made of compatible resins. "Compatible resins" as used herein means that the melting points of the two materials are close enough so that at the operating temperature both form thick, viscous melts which will flow together to form a single melt phase without polymer degradation or formation of thermal or other chemical reaction products which would weaken or otherwise interfere with formation of the single melt phase and its subsequent cooling and solidification to a strong joint. For example, polyethylene is compatible with polyethylene copolymers and polypropylene.

In order to obtain a secure dock, tubes to be joined must not contain more liquid than a thin film on the walls at or near the locations where they are to be cut and joined. Generally, the length of tubing which is empty of liquid need not be more than about 0.5 to 1 inch (13-25 mm).

The apparatus of the invention can form part of a sterile connection system for continuous ambulatory peritoneal dialysis in which a dialysis solution container with a transfer port that includes a segment of tubing is coupled to a tube extending from an implanted catheter opening into a patient's peritoneal cavity. In this embodiment of the invention the patient's tube and/or the transfer tube can have an entry port with a protective cover or a sealed distal end but preferably both have a sealed distal end. This system minimizes the possibility of peritonitis and permits any other treatment bag, such as a bag of antibiotic, bacteriostat, or other medication to be connected as desired. Moreover, this embodiment offers the additional advantage of eliminating the need for the patient to carry the empty dialysis solution bag because the bag can be sterilely disconnected and the patient's tube can be joined to a sterile sealed-end tube. It also eliminates the need for the present laborious procedure used to achieve sterility.

In another embodiment, the apparatus of the invention forms part of a sterile connection system for connecting two blood bags. One of the bags can be a donor bag and the other a transfer bag. The donor bag will have a blood collection tube and optionally can have a transfer port with a transfer tube. The transfer bag has a transfer tube (connection tube). The two bags can be sterilely connected by joining the connection tube of the transfer bag to the transfer port of the donor bag. The transfer port of the donor bag can be a conventional entry port, e.g., having a protective covering and a septum inside the port. The bags can also be connected by joining the blood collection tube of the donor bag to the connection tube of the transfer bag. In another embodiment, the blood collection tube and the connection tube of the transfer bag both have a sealed distal end.

In the preferred embodiment for both the blood bag system and the CAPD system, the donor bag and dialysis bag have, specifically for sterile connection, an additional tube (pigtail) which is connector-free and has a sealed distal end. The term "connector-free" as used herein means the tube does not bear any of the conventional fittings, such as a plastic fitting with a diaphragm, a low-melting thermoplastic insert, an insert fusable by radiant energy, or the like. The tube has a sealed distal end which is prepared solely by sealing the tube end together by use of heat, solvent or the like. Heretofore, there was no known method of sterilely entering or connecting to a bag having such a tube as its only practical means of entry. The tube is equipped with means, such as a clamp, to prevent undesired flow of liquid into said tube.

Figure 10:
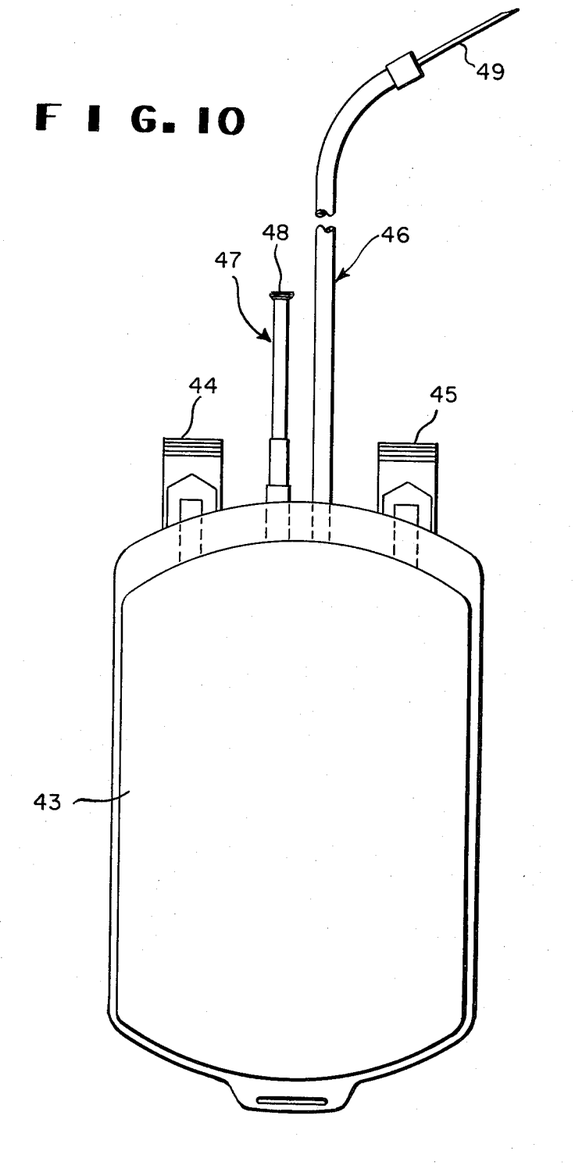
FIG. 10 is a perspective view of a blood bag having a pigtail with a sealed distal end.
Figure 11:
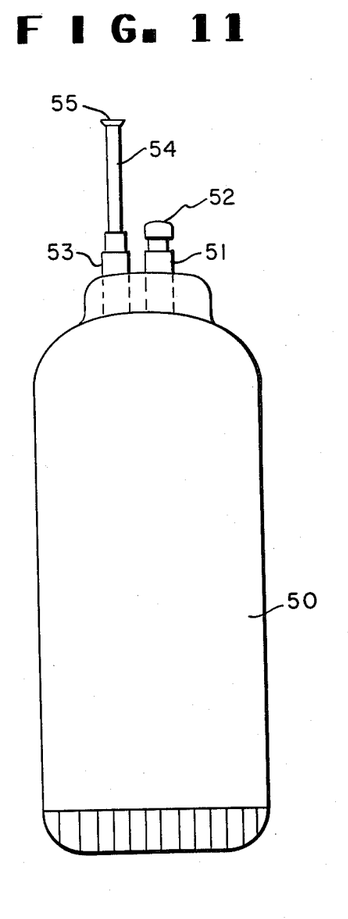
FIG. 11 is a perspective view of a dialysis bag having a pigtail with a sealed distal end.

FIG. 10 shows the blood bag of the invention having conventional access ports 44 and 45, inlet or blood collection tube 46 which is connected to a needle 49 and pigtail 47 having sealed distal end 48. FIG. 11 illustrates the dialysis bag 50 of the invention having conventional filling tube 51 with protective cover 52. Attached to transfer port 53 of bag 50 is pigtail 54 having sealed distal end 55. Pigtail 54 is attached to transfer port 53 by solvent sealing or the like.

In the present system for the sterile connection of blood bags, the need to pre-assemble bags into a system is eliminated. It is to be understood that the expression "blood bag" as used herein refers collectively to either the donor (primary) bag or the satellite bag. With the present invention satellite bags can be sterilely connected to a donor bag as the need arises. The donor bag can be made from a wet-sterilizable material, such as polyvinyl chloride whereas the satellite bags do not have to be wet-sterilizable but can be made of material which can be sterilized only by dry-sterilization means, such as irradiation or ethylene oxide treatment. For example, the satellite bag can be constructed from $O_2$ permeable polyethylene which would increase platelet viability. Alternatively, the satellite bag can be made from a polyethylene copolymer, a polyethylene laminate, polypropylene, or any other material which is compatible with the material from which the donor bag is constructed. The satellite bag can be made from material which is incompatible with the material from which the donor bag is constructed so long as the tubes to be connected are made of compatible materials. For instance, the donor bag and its tubing can be made from polyvinyl chloride whereas the satellite bag can be made from polyethylene but its tubing made from polyvinyl chloride and solvent welded to the satellite bag. Techniques for solvent welding are well known in the art. Supplemental treatments can be sterilely added and washing to remove treating agents can be sterilely effected. Some practitioners believe hepatitis risks can be reduced by washing red cells without previous freezing.

The sterile docking apparatus of the invemtion can also be used to provide a system for producing sterile, non-autoclavable body fluid containers having wet-sterilized (autoclaved) liquid therein. The system is similar to that described in U.S. Pat. No. 4,223,675; however, the present apparatus eliminates the need to have special connectors attached to the tubing.

With the present invention a dry-sterilized package can be formed from a synthetic resin material which is unsuitable for being subjected to wet-sterilization conditions but is particularly suitable for prolonged storage of body fluids. The autoclavable liquid is placed in an autoclavable dispenser equipped with an access tube which can then be heat-sealed closed. The dispenser package and liquid are then wet-sterilized in an autoclave. The dispenser package is next sterilely connected to a dry-sterilized container by using the apparatus and process of the invention. The dry-sterilized container can be equipped with a connector-free tube having a sealed distal end, said tube being specifically for sterile connection. After the sterile connection is made the autoclaved liquid is transferred to the dry-sterilized container which is non-autoclavable. If desired, the two containers can be separated by heat sealing the connecting tube while moving the containers apart so that each container is left with a connector-free tube having a sealed distal end. Other packages can be connected to either container by subsequent sterile docking operations. The autoclavable liquid can be an anticoagulant and the autoclavable dispenser package can be constructed from polyvinyl chloride. The non-autoclavable container can be a blood bag constructed from materials such as those previously described herein.

The process of the invention for joining two thermoplastic tubes together transversely of the axis of each tube comprises forming a continuous molten seal between a heated cutting surface and a transverse section of each said tube whereby maintaining a seal between the interior and exterior of said tubes, joining the respective molten ends of said tubes together to form a joint between said tubes while maintaining said seal, and cooling the resulting joint. As used herein, transverse means crosswise the axis of each tube but not necessarily at right angle with each tube. The process of the invention can be carried out using the herein-described specific embodiment of the apparatus of the invention but is not limited thereto. The conditions of operations are those previously set forth herein.

The invention is further illustrated by the following examples in which all temperatures are in degrees Celsius unless otherwise noted.

EXAMPLE 1

The apparatus used had a pair of aluminum blocks 17 and 18 measuring 1 inch (25 mm) by 2 inches (51 mm) by ½ inch (13 mm). The blocks each had a pair of slots 0.156 inch (4.0 mm) in diameter across their 1 inch (25 mm) surface, and imbedded in the surface to a depth such that a 0.100 inch (2.54 mm) wide opening was left in the surface where the tube was pressed into the slot. The slots were spaced 0.25 inch (6.35 mm) apart, center to center. The blocks were slidably mounted on polytetrafluoroethylene guides in a lower housing which is hingedly attached to an upper housing. The upper housing was fitted with a sharpened 1 inch (25 mm) by 0.5 inch (13 mm) by 0.01 inch (0.25 mm) steel knife blade removably mounted in a 2 inch (51 mm) by 0.7 mm (18 mm) bronze blade holder fitted with a magnet to hold the blade in place which in turn was mounted on a 2.4 inch (61 mm) by 3 inch (76 mm) by 1 inch (25 mm) ceramic block fitted with a 45 watt resistance heater. The tubing ends, 165 mil (4.2 mm) outside diameter, 10 mil (0.25 mm) thick wall plasticized polyvinyl chloride blood bag tubing, were pressed in the slots while aligned as shown in FIG. 1. The blade was heated by the resistance heater to 327° (620° F.). The housing was closed and blocks 17 and 18 were slid to the position shown in FIG. 2 over a period of about a second from start to finish of slide. With no delay, the blocks were moved to the position shown in FIG. 3 in ½ second. The blocks were urged together with a spring as the hot knife blade was being removed from between the blocks in ½ second after a delay of 1 second. The housing was opened and after a delay of 5 seconds the tube was removed. The blade was replaced for the next operation in order to provide a clean blade free of debris from a previous operation. The thusly joined tubes had about 90% of their original strength when pulled in tension. The joints passed a 30 psi pressure test.

EXAMPLE 2

In this Example the connections were tested for sterility. Blood bags fitted with sealed tubes of the size and material used in Example 1 were used in this Example. Approximately 50 mls of sterile nutrient medium were added to blood bags in a laminar flow laboratory hood with other precautions being taken against bacterial contamination. The nutrient medium contained per liter 17 g of tripticase peptone (a pancreatic digest of casein), 3 g of phytone peptone (a digest of soybean meal), 5 g of sodium chloride, 2.5 g of dipotassium phosphate and 2.5 g of dextrose. The bags were incubated at 35° and after 48 hours the nutrient medium was checked for sterility. There was no evidence of contamination. To guarantee that the sterility test was applied to the inside of the tube, the bags were hung upside down during the incubation period so that the broth was in the tube where the joint was to be made. The outside surface of the blood collection bag tubing was coated with an albumin solution to make the tube sticky and coated with bacteria by immersing the sealed ends of the tubes to a depth of about 4 to 6 inches in a dense bacterial spore suspension ($1.8 \times 10^7$ per ml) of *Bacillus subtillus*, variety *niger* (*B. globigii*) before the docking was done.

The *B. globigii* spore suspension described above was applied to the ends of the tubing of a plurality of bags containing the nutrient medium and an equal number of empty bags. The tube joining was performed as described in Example 1. The nutrient medium was kept in contact with the joint and incubated for 48 hours. Then, using sterility precautions similar to those described above, the nutrient medium from each bag set was removed and filtered and the filters were incubated for 48 hours at 35°. All of the filters so incubated were clean with no evidence of a colony of bacteria present, thereby demonstrating that live bacteria had not been introduced into the tube lumen during the docking procedure.

One inch pieces from the cut off end portions of the tubing were placed in a tube containing the same nutrient medium used above and incubated at 35°. After 48 hours each tube of broth was extremely turbid with typical growth of *B. globigii*.

I claim:

1. A process of joining first and second thermoplastic tubes together transversely of the axis of each tube comprising urging a hot cutting means through each tube and simultaneously forming a continuous molten seal between a heated cutting surface and a transverse section of each said tube thereby maintaining a seal between the interior and exterior of said tubes aligning said tubes with each other and, joining the respective molten ends of said tubes together to form a joint between said tubes, both while maintaining said seal.

2. A process of forming a sterile connection between a first tube formed of a thermoplastic resin and a second tube formed of a thermoplastic resin comprising mounting said tubes in a pair of mounting means which hold said tubes in a closely adjacent substantially parallel position, urging an edge of a hot cutting means having substantially flat surfaces through both said tubes at a rate such that the thermoplastic resin from which said tubes are formed which is in contact with said cutting means is molten, whereby a molten interface is formed between the substantially flat surfaces of said cutting means and each of said tubes, maintaining said molten interfaces while aligning said tubes with each other and then passing said tubes over an edge of said cutting means while urging said tubes together, and permitting the thusly joined molten interfaces to cool whereby a sterile connection is formed between said tubes.

3. The process of claim 2 wherein the hot cutting means is maintained at above about 500° F.

4. The process of claim 3 wherein the hot cutting means is maintained at a temperature below the temperature where the thermoplastic resin from which the tubes are made begins to degrade in the time used.

5. The process of claim 4 wherein the mounting means holding the tubes are a pair of blocks having slots therein which hold said tubes.

6. The process of claim 5 wherein the blocks are spaced from about 5 to about 50 mils from said cutting means while the molten interfaces are being formed.

7. The process of claim 6 wherein the blocks are spaced from about 10 to about 20 mils from said cutting means while the molten interfaces are being formed.

8. An apparatus for forming a sterile connection comprising a cutting means, means adapted to heat said cutting means, a pair of mounting blocks adapted to receive and hold two tubes to be joined, means to provide movement between said blocks and said cutting means to a position such that the cutting means is between said blocks and traversing where the blocks are adapted to receive tubes, means adapted to realign said blocks to a position where two different tube ends are aligned with and facing each other and means to separate said blocks and said cutting means while urging said blocks together.

9. An apparatus for forming a sterile connection comprising a cutting means; means adapted to heat said cutting means; a pair of mounting blocks adapted to receive and hold two tubes to be joined; means for movement of the mounting blocks to first, second and third positions, the cutting means being between the mounting blocks in the first position, said mounting blocks being relatively displaced in said second position to align two different tube ends facing each other, said mounting blocks being separated from said cutting means in said third position, and spring means urging said mounting blocks together when in the third position.

10. The apparatus of claim 9 wherein the blocks are spaced from about 5 to about 50 mils from said cutting means when said cutting means is positioned between said blocks.

11. The apparatus of claim 10 wherein the blocks are spaced from about 10 to about 20 mils from said cutting means when said cutting means is positioned between said blocks.

12. A sterile connection system for continuous ambulatory peritoneal dialysis in which a dialysis solution container with a transfer port that includes a segment of tubing is coupled to a tube extending from a patient's peritoneal cavity, wherein the improvement comprises a pair of mounting blocks adapted to receive and hold the transfer port tube and the patient's tube, cutting means, means adapted to heat said cutting means, means to provide movement between said blocks and said cutting means to a position such that the cutting means is between said blocks and traversing where the blocks are adapted to receive said tubes, means to realign said blocks to a position where the different tube ends are aligned with and facing each other, and means to separate said blocks and said cutting means while urging said blocks together.

13. The sterile connection system of claim 12 wherein the patient's tube is connector-free and has a sealed distal end.

14. The sterile connection system of claim 12 wherein the transfer port tube is connector-free, has a sealed distal end, and is the same diameter as that of the patient's tube.

15. A sterile connection system for joining two blood bags, each bag having a tube which can be used for connection and sterile connection being made by joining said tubes, wherein the improvement comprises a pair of mounting blocks adapted to receive and hold the tubes to be joined, cutting means, means adapted to heat said cutting means, means to provide movement between said blocks and said cutting means to a position such that the cutting means is between said blocks and traversing where the blocks are adapted to receive said tubes, means to realign said blocks to a position where the different tube ends are aligned with and facing each other, and means to separate said blocks and said cutting means while urging said blocks together.

16. The sterile connection system of claim 15 wherein one of the bags is a donor bag and its blood collection tube is one of the tubes to be joined.

17. The sterile connection system of claim 16 wherein the two tubes to be joined are of the same diameter.

18. The sterile connection system of claim 17 wherein the blood collection tube has a sealed distal end.

19. The sterile connection system of claim 18 wherein the second bag is a transfer bag having a transfer port with a transfer tube and the transfer tube is the other tube to be joined.

20. The sterile connection system of claim 19 wherein the transfer tube has a sealed distal end.

21. The sterile connection system of claim 15 wherein one of the bags is a donor bag having, in addition to its blood collection tube, a connector-free tube to be used specifically for sterile connection, said tube having a sealed distal end.

22. The sterile connection system of claim 21 wherein the donor bag is steam sterilizable and the other bag is a transfer bag made from material which is dry sterilizable only.

23. The sterile connection system of claim 22 wherein the transfer bag has a connector-free tube having a sealed distal end.

24. The sterile connection system of claim 23 wherein the two tubes to be connected are of the same diameter.

* * * * *

UNITED STATES PATENT AND TRADEMARK OFFICE
CERTIFICATE OF CORRECTION

PATENT NO. : 4,369,779
DATED : January 25, 1983
INVENTOR(S) : Dudley W. C. Spencer It is certified that error appears in the above—identified patent and that said Letters Patent is hereby corrected as shown below:

Column 1, line 60, "scare" should read -- scar --.

Column 6, line 37, "of", first occurrence, should read -- or --.

Column 9, line 26, "whereby" should read -- thereby --.

Column 10, line 61, "tubes aligning" should read -- tubes, aligning --.

Signed and Sealed this

Twenty-fifth Day of October 1983

[SEAL]

Attest:

Attesting Officer

GERALD J. MOSSINGHOFF

Commissioner of Patents and Trademarks